United States Patent [19]

Harada

[11] Patent Number: 4,778,924

[45] Date of Patent: Oct. 18, 1988

[54] PROCESS FOR THE PRODUCTION OF CINNAMIC ACID

[75] Inventor: Haruhisa Harada, Ichihara, Japan

[73] Assignee: Sumitomo Chemical Company, Limited, Osaka, Japan

[21] Appl. No.: 62,405

[22] Filed: Jun. 15, 1987

Related U.S. Application Data

[63] Continuation of Ser. No. 754,889, Jul. 15, 1985.

[30] Foreign Application Priority Data

Jul. 30, 1984 [JP] Japan .................................. 59-161348

[51] Int. Cl.$^4$ ............................................. C07C 51/235
[52] U.S. Cl. ..................................................... 562/421
[58] Field of Search ........................................ 562/421

[56] References Cited

U.S. PATENT DOCUMENTS

| | | | |
|---|---|---|---|
| 3,012,038 | 12/1961 | O'Neill et al. | 562/421 X |
| 3,584,038 | 6/1971 | Barone et al. | 562/421 X |
| 3,919,305 | 11/1975 | Gay | 562/421 |

Primary Examiner—Michael L. Shippen
Attorney, Agent, or Firm—Armstrong, Nikaido, Marmelstein & Kubovcik

[57] ABSTRACT

Cynnamic aldehyde disolved in an aromatic hydrocarbon is oxidized in the liquid phase with molecular oxygen at a temperature in the range of 30°–80° C. in the presence of a cobalt compound and water.

4 Claims, No Drawings

PROCESS FOR THE PRODUCTION OF CINNAMIC ACID

This application is a continuation of application Ser. No. 754,889 filed July 15, 1985.

FIELD OF INVENTION

The present invention relates to a process for producing cinnamic acid which is an industrially important compond as a raw material for perfumes, L-phenylalanine, or the like at a high yield by oxidation of cinnamic aldehyde.

BACKGROUND OF THE INVENTION

Hitherto, cinnamic acid (abbreviated as CA hereinafter) has been produced by a process for reacting benzaldehyde with acetic anhydride in the presence of potassium or sodium acetate, that is, a so-called Perkin process (Organic Reactions, Vol. 1, 217(1942)). The said process is an established one but it has defects that it employs a large amount of expensive acetic anhydride and potassium or sodium acetate, requires a precipitating process with an acid and a recrystallization process after the reaction, and produces waste water.

On the other hand, a process for the production of CA by the liquid-phase oxidation of cinnamic aldehyde (abbreviated as CAL hereinafter) prepared by the condensation reaction of benzaldehyde with acetaldehyde in an aqueous caustic soda solution using molecular oxygen in the presence of silver oxide catalyst is a publicly-known process disclosed in U.S. Pat. No. 3,162,682 and in British Pat. No. 782430. The said process has, however, defects that it employs expensive silver oxide as the catalyst and requires the reaction temperature to be maintained at 30° C. or lower (because a silver mirror reaction occurs, causing a catalyst loss, if its reaction temperature exceeds 30° C.). In addition, the said process requires a precipitating process with an acid and a recrystallization process and also produces waste water, as in the Perkin reaction.

The inventors have devoted themselves to studies on a process for preparation of CA by oxidation of CAL which does not have the above-mentioned defects and as a result, have found that, if CAL dissolved in an aromatic hydrocarbon is subjected to a liquid-phase oxidation reation employing molecular oxygen in a reaction system consisting of the said solution and coexisting water in the presence of a cobalt compound catalyst, CAL is converted into CA at a high yield, the reaction system is separated into an aqueous layer and an oil layer, and high-purity CA crystals are obtained readily by cooling the oil layer. Further, they have found that the said aqueous layer contains the catalyst dissolved in it and can be recycled for use and thus they have completed the invention.

The invention is a process for the production of cinnamic acid by the oxidation reaction of cinnamic aldehyde characterized in that cinnamic aldehyde dissolved in an aromatic hydrocarbon is oxidized in a liquid phase using molecular oxygen in the coexistence of a cobalt catalyst and water.

DETAILED DESCRIPTION OF THE INVENTION

As the aromatic hydrocarbon for use in the method of the invention, the ones represented by the following general formula (I) are all usable. However benzene, toluene, xylene, and polymethylbenzenes which are strong in an oxidizing atmosphere are particularly preferred,

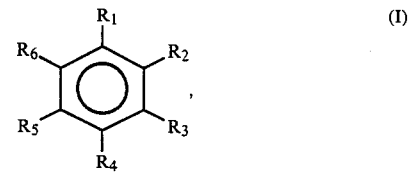

where $R_1$, $R_2$, $R_3$, $R_4$, $R_5$, and $R_6$ each are hydrogen atom or an alkyl group of 1-4 carbon atoms.

The ratio of CAL to the said aromatic hydrocarbon varies more or less with the solubility of the product CA in the said aromatic hydrocarbon but the concentration range of CAL of 10-50 wt % is selected. It is because the oxidation reaction becomes inefficient with a CAL concentration less than 10 wt % and the product CA ma precipitate during the oxidation reaction with a CAL concentration exceeding 50 wt %. Characteristics of the method of the invention reside in the coexistence of water in the reaction system and in the use of a cobalt compound as the catalyst. The method of the invention is characterized in that the coexistence of water results in improvement in selectivity for the product CA and results in easy separation of the catalyst. The suitable range of the amount of coexisting water is 10-200 parts by weight based on 100 parts of aromatic hydrocarbon dissolving CAL, and separation of the catalyst becomes difficult with an amount of the coexisting water less than 10 parts by weight and the said amount exceeding 200 parts by weight becomes disadvantageous in repect of product yield.

On the other hand, as the cobalt compound, all cobalt compounds are essentially usable. Water soluble cobalt salts, however, are particularly preferable when separation of the catalyst and the like are taken into account and specifically, there may be mentioned cobalt acetate, cobalt benzoate, cobalt stearate, cobalt bromide, and the like as the catalyst. The amount of the catalyst added is selected in a range of 0.1-20% by weight based upon the concentration in an aqueous solution of the catalyst in water. When the said concentration is less than 0.1% by weight, the effect of catalyst is low and when the said concentration exceeds 20% by weight, the conversion ratio of CAL is lowered and at the same time, the selectivity for the product CA is also lowered. In addition, the aqueous phase containing the catalyst can be recycled for use.

The reaction temperature is selected in a range of 30°-80° C. and when the reaction temperature is lower than 30° C., the reaction velocity is small and further, the product CA may be precipitated. When the reaction temperature exceeds 80° C., the selectivity for CA is markedly lowered, so that such a high reaction temperature is not preferred.

The reaction pressure is selected generally in a range of normal pressure to 20 kg/cm$^2$G. By cooling the aromatic hydrocarbon solvent containing CA produced by the oxidation reaction of CAL in accordance with the method of the invention, and by further cooling the said aromatic hydrocarbon solvent after being concentrated as required, it has become possible to obtain high-purity CA crystals by one step without the necessity of performing a precipitation process with an acid and a recrystallization process. Further, the oxidation reaction in the method of the invention can be carried out batchwisely and also continuously.

The invention will be described in detail in examples hereinafter.

EXAMPLE 1

15 g of CAL, 45 g of toluene, 60 g of water and 0.5 g of cobalt acetate were charged into a three-necked round-bottom flask having a capacity of 200 ml and the mixture was reacted at 40° C. for 8 hours blowing air into the reaction mixture at a rate of 100 cc/min. After completion of the reaction, the toluene phase was separated from the water phase without being cooled and then when the toluene phase was cooled, CA crystals precipitated. After being separated by filtration, the CA crystals were dried with air and the purity of CA crystals was determined by gas chromatography and by GPC* measurement. The reaction results and the purity of CA are shown in Table-1. (*: Gel permutation chromatography)

EXAMPLES 2-5

Oxidation of CAL was carried out in Examples 2-5 by the same method as in Example 1 except that, instead of cobalt acetate in Example 1, cobalt benzoate was used (in Example 2), cobalt stearate was used (in Example 3), cobalt bromide was used (in Example 4) and cobalt (II) acetylacetonate was used (in Example 5). The results are shown in Table-1.

COMPARATIVE EXAMPLE 1

Oxidation of CAL was carried out by the same method as in Example 1 except that no catalyst was used. The results are shown in Table-1.

The results of Table-1 indicate clearly that the method of the invention is superior to the oxidation reaction system employing no catalysts.

TABLE 1

| Example | Catalyst | CAL conv.(%) | CA select.(%) | CA crystal purity(%) |
| --- | --- | --- | --- | --- |
| 1 | Co acetate | 53.6 | 80.1 | 99.8 |
| 2 | Co benzoate | 58.2 | 79.3 | 99.2 |
| 3 | Co stearate | 51.3 | 78.4 | 99.1 |
| 4 | Co bromide | 56.4 | 75.2 | 99.4 |
| 5 | Co acetylacetonate | 53.1 | 80.5 | 99.6 |
| Comparat. example 1 | No catalyst | 26.2 | 37.3 | 92.8 |

EXAMPLES 6-7

Oxidation of CAL was carried out in Examples 6 and 7 by the same method as in Example 1 except that, instead of toluene in Example 1, benzene was used (in Example 6) and p-xylene was used (in Example 7). The reaction results and the purity of the resulting CA crystals are shown in Table-2.

COMPARATIVE EXAMPLE 2

15 g of CAL, 60 g of water, and 0.5 g of cobalt acetate were charged into a three-necked round flask and no aromatic hydrocarbon solvent was added to the reaction system. After that, oxidation of CAL was carried out by the same method as in Example 1. The results are shown in Table-2.

COMPARATIVE EXAMPLE 3

15 g of CAL, 45 g of toluene, and 0.5 g of cobalt acetate were charged into a three-necked round flask and no water was added to the reaction system. After that, oxidation of CAL was carried out by the same method as in Example 1. The results are shown in Table-2.

TABLE 2

| | Solvent | Presence of water | CAL conv.(%) | CA select.(%) | CA crystal purity(%) |
| --- | --- | --- | --- | --- | --- |
| Example 6 | Benzene | Present | 57.8 | 81.2 | 99.8 |
| Example 7 | p-xylene | Present | 56.2 | 80.5 | 99.1 |
| Comp. exa. 2 | No solvent | Present | 26.7 | 28.8 | Not precipitate |
| Comp. exa. 3 | Toluene | Not present | 52.8 | 32.5 | 80.5 |

The results of Table-2 indicate clearly the effect of coexistence of solvent and water.

EXAMPLE 8

60 g of the separated water phase obtained in Example 1 was reused and the said separated water phase, 15 g of CAL, and 45 g of toluene were charged into a three-necked round flask. After that, oxidation of CAL was carried out by the same method as in Example 1. The reaction results and the purity of CA crystals obtained are shown in Table-3 and compared with results of Example 1.

TABLE 3

| | CAL conversion(%) | CA selectivity(%) | CA crystal purity(%) |
| --- | --- | --- | --- |
| Example 1 | 53.6 | 80.1 | 99.8 |
| Example 8 | 52.8 | 80.0 | 99.3 |

While the invention has been described in detail and with reference to specific embodiments thereof, it will be apparent to one skilled in the art that various changes and modifications can be made therein without departing from the spirit and scope thereof.

What is claimed is:

1. A process for the production of cinnamic acid comprising oxidizing with molecular oxygen, cinnamic aldehyde dissolved in an aromatic hydrocarbon represented by the following formula (I), said oxidation being carried out in a liquid phase with molecular oxygen at a temperature in the range of 30°-80° C. in the presence of a cobalt compound and water, the water being present in the amount of from 10 to 200 parts by weight per 100 parts by weight of the aromatic hydrocarbon dissolving the cinnamic aldehyde, so that the reaction system consists of an aqueous layer and an oil layer, formula (I) being:

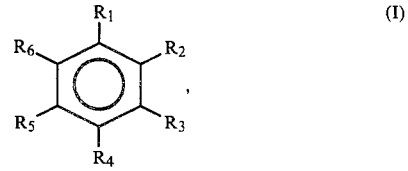

where $R_1$–$R_6$ each are hydrogen or an alkyl group of 1-4 atoms.

2. A process for the production of cinnamic acid as set forth in claim 1 characterized in that the aromatic hydrocarbon is benzene, toluene or xylene.

3. A process for the production of cinnamic acid as set forth in claim 1 characterized in that the cobalt compound is a water soluble cobalt salt.

4. A process for the production of cinnamic acid as set forth in claim 3 characterized in that the water soluble cobalt salt is cobalt acetate, cobalt benzoate, cobalt stearate or cobalt bromide.

* * * * *